(12) United States Patent
Lin et al.

(10) Patent No.: US 9,662,350 B2
(45) Date of Patent: May 30, 2017

(54) PHARMACEUTICAL COMPOSITION AND METHOD FOR INHIBITING INFLAMMATION

(71) Applicant: CHINA MEDICAL UNIVERSITY, Taichung (TW)

(72) Inventors: Feng-Huei Lin, Taichung (TW); Teng-Le Huang, Taichung (TW); Horng-Chaung Hsu, Taichung (TW); Chun-Hsu Yao, Taichung (TW); Yueh-Sheng Chen, Taichung (TW); Wen-Yu Su, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 144 days.

(21) Appl. No.: 14/452,836

(22) Filed: Aug. 6, 2014

(65) Prior Publication Data

US 2015/0094279 A1 Apr. 2, 2015

Related U.S. Application Data

(62) Division of application No. 13/336,178, filed on Dec. 23, 2011, now Pat. No. 8,835,405.

(30) Foreign Application Priority Data

Sep. 16, 2011 (TW) .............................. 100133355 A

(51) Int. Cl.
| | |
|---|---|
| *A61K 31/728* | (2006.01) |
| *A61K 9/00* | (2006.01) |
| *A61K 31/355* | (2006.01) |
| *A61K 31/375* | (2006.01) |
| *A61K 31/59* | (2006.01) |
| *A61K 47/02* | (2006.01) |

(52) U.S. Cl.
CPC .......... *A61K 31/728* (2013.01); *A61K 9/0019* (2013.01); *A61K 31/355* (2013.01); *A61K 31/375* (2013.01); *A61K 31/59* (2013.01); *A61K 47/02* (2013.01)

(58) Field of Classification Search
None
See application file for complete search history.

(56) References Cited

U.S. PATENT DOCUMENTS

| | | | | |
|---|---|---|---|---|
| 2005/0182022 | A1* | 8/2005 | Pierce | A61K 31/728 514/54 |
| 2008/0044476 | A1* | 2/2008 | Lyons | A61K 9/0019 424/488 |
| 2011/0117207 | A1* | 5/2011 | Minatelli | A23L 1/2753 424/581 |

FOREIGN PATENT DOCUMENTS

WO WO 2008154178 A1 * 12/2008 ............... A23L 1/30

OTHER PUBLICATIONS

Forbes, RFA Vitamin Conversion Chart. Robert Forbes & Associates Pty Ltd. 2008.*
Institute of Medicine of the National Academies, Dietary Reference Intakes for Calcium and Vitamin D. Washington, DC: The National Academies Press, 2010.*

* cited by examiner

*Primary Examiner* — Shaojia Anna Jiang
*Assistant Examiner* — Dale R Miller
(74) *Attorney, Agent, or Firm* — Grossman, Tucker, Perreault & Pfleger, PLLC

(57) ABSTRACT

A pharmaceutical composition for inhibiting inflammation is provided. The pharmaceutical composition comprises (a) hyaluronic acid, (b) a vitamin and (c) a pharmaceutically acceptable carrier.

5 Claims, 3 Drawing Sheets

PHARMACEUTICAL COMPOSITION AND METHOD FOR INHIBITING INFLAMMATION

CROSS-REFERENCE TO RELATED APPLICATIONS

This application is a divisional application of U.S. application Ser. No. 13/336,178 filed Dec. 23, 2011 which claims the benefit of Taiwan Patent Application No. 100133355, filed on Sep. 16, 2011, in the Taiwan Intellectual Property Office, the disclosures of which are incorporated herein in their entirety by reference.

BACKGROUND OF THE INVENTION

Field of the Invention

The present invention relates to a pharmaceutical composition for inhibiting inflammation, especially to a pharmaceutical composition useful for arthritis.

Descriptions of the Related Art

Arthritis is a common chronic disease that leads to joint ache due to the degeneration of articular cartilage or the inflammation of connective tissue, and thus, affects the normal movement of the joint. According to the location and causes of the occurrence, arthritis can be classified into more than a hundred types. The most common types comprise osteoarthritis (degenerative arthritis), rheumatoid arthritis, gouty arthritis, bacterial arthritis, ankylosing spondylitis, and lupus erythmatosus.

With regards to the therapy of arthritis, the initial therapy generally adopts conservative and non-surgical methods, such as medicine treatments and injection treatments. When the initial therapy is ineffective, a surgical operation treatment will then be adopted. It has been known that medicine treatments comprise the use of steroidal anti-inflammation drugs and non-steroidal anti-inflammation drugs. Although steroidal anti-inflammatory drugs can provide a quick and effective analgesic effect, the drugs cause many side effects, such as osteoporosis, uncicatrized wounds, upper gastrointestinal bleeding, or may even aggravate the symptoms of hypertension or diabetes. Thus, these drugs are gradually excluded in the medicine treatment. As for non-steroidal anti-inflammation drugs, although they can provide a good analgesic effect, if used long term, side effects, such as peptic ulcer, lower limb dropsy, damage of kidney function, etc., may arise. Thus, non-steroidal drugs are restricted in practical application.

It has been known that hyaluronic acid (also known as hyaluronan or alduronic acid) has been widely used in injection formulations for inhibiting osteoarthritis. In this case, an injection solution containing hyaluronic acid is directly injected into a patient's joint to moderately alleviate inflammation and relive the achy feeling. The mechanism of hyaluronic acid is still unclear to date, but it has been known that hyaluronic acid also can act as a lubricant to help the movement of joints, and meanwhile, improve joint function. However, it has been discovered that although hyaluronic acid can effetely relieve ache, when entering the human body, it is possible to induce temporary inflammatory responses within several days, or even may cause chronic inflammation (see Leopold et al., Increased frequency of acute local reaction to intra-articular hylan GF-20 (Synvisc) in patients receiving more than one course of treatment. J Bone Joint Surg, 2002; 84: 1619-23; Bernardeau et al., Acute arthritis after intra-articular hyaluronate injection: onset of effusions without crystal. Ann Rheum Dis, 2001; 60:518-20; and Kroesen et al., Induction of an acute attack of calcium pyrophosphate dihydrate arthritis by intra-articular injection of hylan G-F 20 (Synvisc). Clin Rheumatol, 2000; 19:147-9, which are entirely incorporated hereinto by reference). Therefore, if a desired anti-inflammation effect can be provided by a lower dosage of hyaluronic acid, the subsequent inflammation responses induced after hyaluronic acid enters a human body can be alleviated or even can be avoided.

A method for improving a hyaluronic acid formulation has been reported. In this method, by using a chemical synthesis method, hyaluronic acid is linked to methotrexate (MTX) with anti-inflammation activity via a polypeptide to form a conjugate, and the resultant product has improved anti-inflammation effects (see Homma et al., Novel hyaluronic acid-methotrexate conjugates for osteoarthritis treatment, Bioorganic and Medicinal Chemistry, 17 (2009), 4647-4656, which is entirely incorporated hereinto by reference). However, according to the teaching of the document, a mixture obtained by simply mixing hyaluronic acid and methotrexate cannot achieve the improving effect; in other words, the synthesis of the conjugate is necessary. However, the preparation of the conjugate needs a polypeptide material and involves complicated synthesis steps, which must increase the production cost of a hyaluronic acid formulation. Thus, this method not only has difficulty in a manufacturing-scale preparation process, but also increases the economic burden of users, and accordingly, has many limitations in clinical application.

The inventors of the present invention found that a combination of vitamin and hyaluronic acid can provide an improved anti-inflammation effect, and thus, a desired anti-inflammation effect can be provided by a lower dosage of hyaluronic acid, thereby alleviating or avoiding the temporary inflammation responses induced after hyaluronic acid enters the human body.

SUMMARY OF THE INVENTION

The primary objective of this invention is to provide a pharmaceutical composition for inhibiting inflammation, comprising: (a) hyaluronic acid; (b) a vitamin and; and (c) a pharmaceutically acceptable carrier.

Another objective of this invention is to provide a method for inhibiting inflammation in a subject, comprising administrating to the subject an effective amount of a composition comprising hyaluronic acid and a vitamin.

Yet another objective of this invention is to provide a kit for inhibiting inflammation, comprising a first part that contains an effective amount of hyaluronic acid, and a second part that contains an effective amount of a vitamin.

The detailed technology and preferred embodiments implemented for the subject invention are described in the following paragraphs accompanying the appended drawings for people skilled in this field to well appreciate the features of the claimed invention.

DETAILED DESCRIPTION OF THE INVENTION

Figure 1:
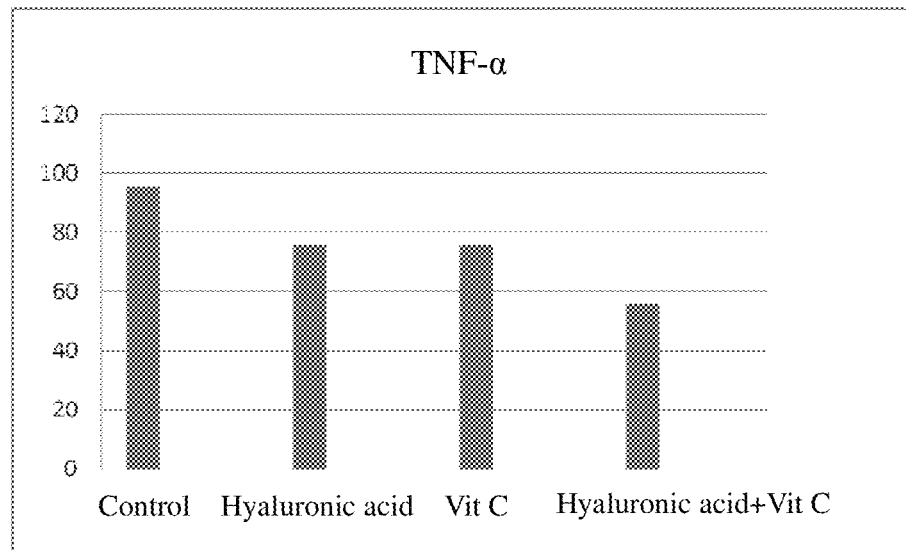
FIG. 1 is a statistic column diagram showing the expression level of the inflammation mediator, tumor necrosis factor-α (TNF-α), in the fibroblast-like synoviocytes treated by vitamin C.

Unless otherwise stated herein, the terms "a (an)", "the" or the like used in this specification (especially in the Claims hereinafter) shall be understood to encompass both the singular and plural form.

As stated above, after hyaluronic acid enters the human body, it sometimes may induce temporary inflammation responses within a few days, or even may cause chronic inflammation, thereby, adversely influencing the anti-inflammation effect thereof. In another aspect, the improved method proposed in the document for preparing a conjugate of hyaluronic acid and methotrexate has a lot of limitations. Through the combination of hyaluronic acid and vitamin, the present invention improves the disadvantages of conventional hyaluronic acid formulations using a simple approach.

Therefore, the present invention provides a pharmaceutical composition for inhibiting inflammation, comprising (a) hyaluronic acid; (b) a vitamin; and (c) a pharmaceutically acceptable carrier.

Hyaluronic acid is one of the major components in the extracellular matrix, and is widely distributed in the endothelial tissue, connective tissue, epidermal tissue, and nervous tissue. Hyaluronic acid is also critical to the physiological activity of cells, like proliferation, migration, etc. In addition, because hyaluronic acid is an important humidifying ingredient in the dermis of the skin and has an excellent viscosity and elasticity, it is an ideal filler and is commonly used in cosmetic products and plastic surgeries.

Hyaluronic acid is a glycosaminoglycan without sulfur. The basic structure of hyaluronic acid is a large polysaccharide composed of two disaccharide units, D-glucuronic acid and N-acetylglucosamine, and has a chemical structure of the following formula (I):

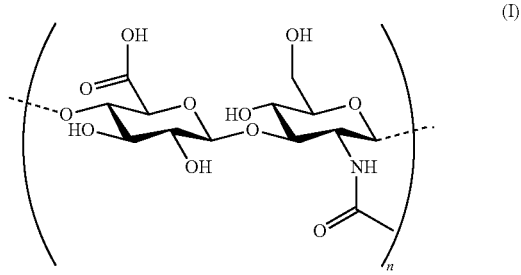

Hyaluronic acid can be prepared from natural materials. For example, it can be extracted from cockscomb, umbilical cord, cartilage, skin, etc. It also can be produced by chemical synthesis or by cultivation or genetic engineering using microorganisms like yeast and so on. Commercial hyaluronic acid formulations also can be used as the source of hyaluronic acid in the pharmaceutical composition of the present invention, for instance, a formulation comprising a hyaluronic acid sodium water solution, such as ARTZ Dispo®, SYNVISC®, HYALGAN®, ORTHOVISC®, etc.; or a formulation comprising a water solution of cross-linked hyaluronic acid derivatives, such as SYNVISC® and DUROLANE®.

There is no a particular limit for hyaluronic acid (component (a)) in the pharmaceutical composition of the present invention, but the average molecular weight of hyaluronic acid is preferably about 30 KDa to about 10,000 KDa, and more preferably about 500 KDa to about 6,000 KDa. In addition, hyaluronic acid can be in an ionic form (i.e., without forming a salt) or in a form of a pharmaceutically acceptable salt. The pharmaceutically acceptable salts of hyaluronic acid comprise salts formed by a combination of hyaluronic acid with an inorganic base (e.g., alkali metal ion salts such as sodium salts or potassium salts; alkali earth metal ion salts, such as magnesium salts or calcium salts; ammonium salt, etc.); or salts formed by the combination of hyaluronic acid with an organic base (e.g., diethanolamine, cyclohexylamine, amino acids, etc.).

Vitamins are micronutrients essential for living organisms. Vitamins cannot be produced by living organisms themselves and must be obtained from exterior sources, such as diet. Although vitamins cannot produce energy in the living organism like carbohydrates, protein and fat, they has an important regulation function in the metabolism of the organism. As shown in the following examples, the inventors of the present invention found that, compared with the individual administration of vitamin or hyaluronic acid, the combination of hyaluronic acid and vitamin can surprisingly provide an improved anti-inflammation effect. Therefore, the combination of hyaluronic acid and vitamin can provide a desired anti-inflammation effect by a lower dosage of hyaluronic acid, thereby, alleviating or even avoiding the subsequent inflammation responses induced after hyaluronic acid enters the human body.

Component (b) in the pharmaceutical composition of the present invention is preferably a vitamin selected from a group consisting of vitamin A, vitamin B, vitamin C, vitamin D, vitamin E, and combinations thereof. More preferably, component (b) is selected from a group consisting of vitamin C, vitamin D, vitamin E, and combinations thereof.

In the pharmaceutical composition of the present invention, there is no a particular limit on the content ratio of component (a) to component (b). When component (b) is at least one of vitamin C or vitamin E, component (a) and component (b) are usually present at a weight ratio of component (a)/component (b)=about 1/1 to about 1,000/1, and preferably are present at a weight ratio of component (a)/component (b)=about 1/1 to about 10/1. When component (b) is vitamin D, component (a) and component (b) are usually present at a weight ratio of component (a)/component (b)=about 1,000/1 to about 100,000/1, and preferably are present at a weight ratio of component (a)/component (b)=about 8,000/1 to about 15,000/1.

The pharmaceutical composition of the present invention can be used in both veterinary and human medicine, and it can be in any suitable form and can be applied by any suitable manner without particular limits. For example, but not limited thereby, the pharmaceutical composition can be applied by oral administration, subcutaneous injection, intravenous injection, or intra-articular injection, etc. Depending on the form and purpose of the pharmaceutical composition of the present invention, the pharmaceutical composition may comprise a pharmaceutically acceptable carrier as component (c).

In terms of the manufacturing of a medicament suitable for oral administration, the pharmaceutical composition of the present invention can comprise a pharmaceutically acceptable carrier which has no adverse influence on the activity of hyaluronic acid and vitamin, such as solvents, oily solvents, thinners, stabilizers, absorption delaying agents, disintegrants, emulsifiers, antioxidants, binders, lubricants, moisture absorbents, etc. The pharmaceutical composition can be prepared in a form suitable for oral administration by any suitable approach, such as a tablet, a capsule, a granule, powder, a fluid extract, a solution, syrup, a suspension, an emulsion, a tincture, etc.

As for a medicament suitable for subcutaneous, intravenous, or intra-articular injection, the pharmaceutical composition of the present invention can comprise one or more additives, such as a pH adjusting agent, an isotonic reagent, a stabilizer (such as sodium bisulfate, dihydrogen sodium sulphate, sodium dihydrogen phosphate, phosphoric acid hydrogen sodium or sodium chloride, etc.), an isotonic solution, an injection water, a saline buffer solution, or a salt buffer (such as a phosphate buffer solution or a citrate buffer solution), etc., to produce an intravenous injection, an emulsion intravenous injection, a powder injection, a suspension injection, a powder-suspension injection, etc.

Optionally, other additives, such as a flavoring agent, a toner, a coloring agent, etc., can be added to the pharmaceutical composition of the present invention to enhance the taste and visual appeal of the composition. A suitable amount of a preservative, a conservative, an antiseptic, an anti-fungus reagent, and so on, also can be added to improve the storability of the resultant medicament.

The pharmaceutical composition may optionally comprise one or more other active components to enhance the effect of the medicament or increase the flexibility for the formulation. For example, one or more active components, such as steroidal anti-inflammation drugs, non-steroidal anti-inflammation drugs, glucosamine, and other active components, etc., can be incorporated into the pharmaceutical composition of the present invention, as long as the other active components have no adverse effect on hyaluronic acid and vitamin.

Because the pharmaceutical composition of the present invention can provide an improved anti-inflammation effect, it can be used for inhibiting inflammation, especially for inhibiting arthritis, such as osteoarthritis (degenerative arthritis), rheumatoid arthritis, gouty arthritis, bacterial arthritis, ankylosing spondylitis, lupus erythmatosus, etc., and preferably can be used for inhibiting osteoarthritis and rheumatoid arthritis. In one embodiment of the present invention, the pharmaceutical composition of the present invention is prepared in an injection formulation form for a treatment method using intra-articular injection.

Compared with conventional hyaluronic acid formulations that cannot provide a significant curative effect on rheumatoid arthritis, one of the advantages of the pharmaceutical composition of the present invention is that it can provide an excellent inhibitory effect on rheumatoid arthritis by inhibiting the secretion of the tumor necrosis factor (TNF, which is an important pathogenic factor of rheumatoid arthritis) from the synoviocyte of the knee joint, and thus, it can be used for curing rheumatoid arthritis. In addition, the pharmaceutical composition of the present invention also can provide an anti-inflammation effect by inhibiting Interleukin-1 (IL-1). Over recent years, degenerative arthritis has been recognized as a non-classical inflammatory disease, and the progress of degenerative arthritis also can be impeded by inhibiting Interleukin-1, thereby, achieving the purpose of changing the nature disease history of degenerative arthritis.

In addition, the pharmaceutical composition of the present invention can not only effectively relieve joint ache and improve joint movement of the patient, but also prevent the progression of arthritis. Moreover, unlike the conventional combination of hyaluronic acid and methotrexate, which forms a conjugate through a complicated approach using a polypeptide to provide a desired anti-inflammation effect, the pharmaceutical composition of the present invention is produced by simply mixing hyaluronic acid and vitamins. Thus, the present invention has the advantages of a simple preparation process and suitability for large-scale manufacturing.

Because the pharmaceutical composition of the present invention can improve the defects of the conventional hyaluronic acid formulations, it can be applied in any known applications of hyaluronic acid, not limited to anti-arthritis. For example, the pharmaceutical composition of the present invention can be applied in cosmetic products and plastic surgeries. For instance, it can be added to a skin care product or a facial injection formulation of hyaluronic acid.

The present invention also provides a method for inhibiting inflammation, comprising administrating to a subject an effective amount of (a) hyaluronic acid and (b) a vitamin. The method of the present invention especially can be used for inhibiting osteoarthritis, rheumatoid arthritis, or gouty arthritis. The species, properties, sources, ratio, dosage form, and administration method of hyaluronic acid and the vitamin are described on above. In one embodiment of the present invention, the pharmaceutical composition of the present invention is injected in an injection formulation form to a joint of the patient to achieve the effect of curing arthritis.

The present invention also provides a kit for inhibiting inflammation, comprising a first part that contains an effective amount of hyaluronic acid, and a second part that contains an effective amount of a vitamin. The species, properties, sources, and ratio of hyaluronic acid and the vitamin are described above.

In the kit of the present invention, there is no particular limit on the form of the first part and the second part. For example, in the kit for intra-articular injection, the first and second parts can be in solution form and are separately placed in independent antiseptic packs (such as plastic bottles or glass bottles like ampoules). Each pack can comprise multiple dosages, but preferably a single dosage, of the first or second part. Herein, the first and second parts are preferably in solution form suitable for injection, and the kit of the present invention can further comprise an injection syringe (such as a disposable injection syringe), or can optionally further comprise an instruction. When an intra-articular injection is performed, the two parts can be put into the injection syringe according to the information in the instruction (comprising the information such as the operation method of the kit, the mixing ratio of the solutions, etc.) to apply the formulation.

In another aspect, in the kit for oral administration, the first and second parts can be independently in the form of a tablet or a capsule, and the two parts can be separately placed in different packages with a single or multiple dosages. Herein, the kit of the present invention can optionally comprise an instruction. When an oral administration is carried out, the two parts can be combined and administrated according to the information of the instruction (comprising information such as the administration regimen, the recommended dosage, etc.).

The detailed technology and preferred embodiments implemented for the present invention are described in the following paragraphs; however, the scope of the present invention is not limited thereby.

[Preparation Example] Preparation of Hyaluronic Acid Intra-Articular Injection

In a pre-loaded hyaluronic acid injection syringe, 1 ml isotonic solution of hyaluronic acid (with a concentration of 0.5 to 2 mg/ml, and an average molecular weight of 600 to 800 KDa) and 0.01 mg to 1 mg vitamin C or vitamin E, or $10^{-4}$ to $10^{-5}$ mg vitamin D were added. A total amount of 5 mg to 20 mg sodium chloride, sodium hydrogen sulfate, and sodium dihydrosulphate were added to the syringe. Finally, 2 ml injection water was added as an excipient to obtain a hyaluronic acid intra-articular injection solution. The solution was stored in the dark at 4° C.

[Example 1] Cell Analysis of the Hyaluronic Acid Intra-Articular Injection Solution Experiment A. Cell Culture The fibroblast-like synoviocytes (FLS) from five patients with degenerative arthritis were collected and cultured. First, the joint synovium of the patients were cut into small pieces, suspended in a DMEM (Dulbecco modified eagle's medium) culture medium, and incubated under an environment of 37° C. and 5% $CO_2$ for 3 days. The culture medium contains 1.5 g/L sodium bicarbonate (S6297, Sigma-Aldrich, St Louis, Mo., USA), 1% penicillin-streptomycin-neomycin (P408, Sigma-Aldrich), and 10% fetal bovine serum (04-001-1A, Biological Industries, Grand Island, N.Y., USA).

Non-attached cells were removed by a phosphate buffered saline solution (PBS), the culture medium was refreshed, and the attached cells were cultured for 2 weeks. After the above steps were repeated 3 to 6 times, the remaining cells were fibroblast-like synoviocytes. The obtained cells were then used for the following test.

Experiment B. Cell Treatment

The fibroblast-like synoviocytes obtained form Experiment A were cultured in a serum-free culture medium for 24 hours. Then, the fibroblast-like synoviocytes were separately cultured in the following four culture medium for 24 hours: (1) a DMEM culture medium comprising only 10% fetal bovine serum (as a control group); (2) a DMEM culture medium comprising 10% fetal bovine serum and hyaluronic acid (having an average molecular weight of 600 KDa to 800 KDa); (3) a DMEM culture medium comprising 10% fetal bovine serum and vitamin C, vitamin D, or vitamin E; and (4) a DMEM culture medium comprising 10% fetal bovine serum, hyaluronic acid (having an average molecular weight of 600 KDa to 800 KDa), and vitamin C, vitamin D or vitamin E. The concentrations of hyaluronic acid and vitamin in the above four culture mediums were the same as the above Preparation Example.

Then, the cells of the aforesaid four groups were collected and centrifuged, and the supernatants were collected for the following analysis.

Experiment C. Quantification of Proteins Related to Arthritis

The inflammation reaction is a complicated procedure, comprising the production of free radical molecules (such as nitric oxide and hydrogen peroxide, etc.), and cytokines (such as prostaglandin E2 (PGE2), tumor necrosis factor-α (TNF-α), Interferon-γ (TNF-γ), Interleukin-2 (IL-2), Interleukin-1β (IL-1β), etc.). Therefore, through the quantification of inflammation-related free radical molecules or cytokines, the inflammation level can be determined.

In this experiment, the concentrations of two cytokines related to degenerative arthritis in the collected supernatants from Experiment B were determined by using a sandwich binding protein assay kit (or sandwich ELISA kits, purchased from the eBioscience company) based on the standard curves according to the manufacturer's manual to analyze the expression level of these cytokines and determine the inflammation level of the cells. The two cytokines were tumor necrosis factor-α (a standard, 88-7340, is purchased from the eBioscience company) and Interleukin-1β (a standard, 88-7010, is purchased from the eBioscience company). Each sample was analyzed twice, and an enzyme-linked immunosorbent assay (ELISA) reader (Sunrise Remote, TECAN) was used to carry out the measurement. The results are shown in Tables 1 to 3 and FIGS. 1 to 6.

TABLE 1

| average concentration (pg/ml) | group | | | |
|---|---|---|---|---|
| | control | hyaluronic acid | vitamin C | hyaluronic acid + vitamin C |
| TNF-α | 95.57 | 75.64 | 75.56 | 56.02 |
| IL-1β | 91.98 | 78.79 | 77.00 | 54.38 |

TABLE 2

| average concentration (pg/ml) | group | | | |
|---|---|---|---|---|
| | control | hyaluronic acid | vitamin D | hyaluronic acid + vitamin D |
| TNF-α | 106.78 | 82.52 | 79.52 | 48.28 |
| IL-1β | 97.47 | 76.03 | 74.78 | 48.05 |

TABLE 3

| average concentration (pg/ml) | group | | | |
|---|---|---|---|---|
| | control | hyaluronic acid | vitamin E | hyaluronic acid + vitamin E |
| TNF-α | 98.09 | 79.28 | 77.03 | 48.28 |
| IL-1β | 97.37 | 78.33 | 75.57 | 48.31 |

[Analysis Result]

Figure 2:
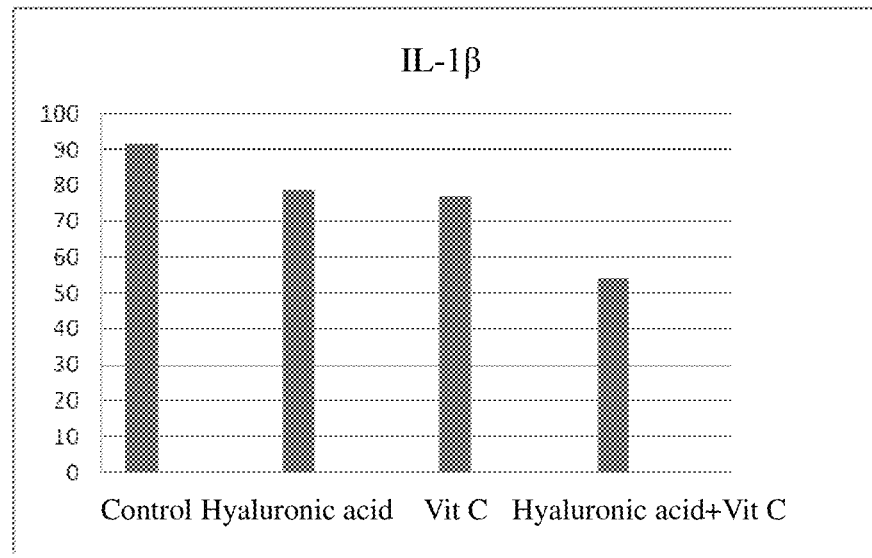
FIG. 2 is a statistic column diagram showing the expression level of the inflammation mediator, Interleukin-1β (IL-1β), in the fibroblast-like synoviocytes treated by vitamin C.
Figure 3:
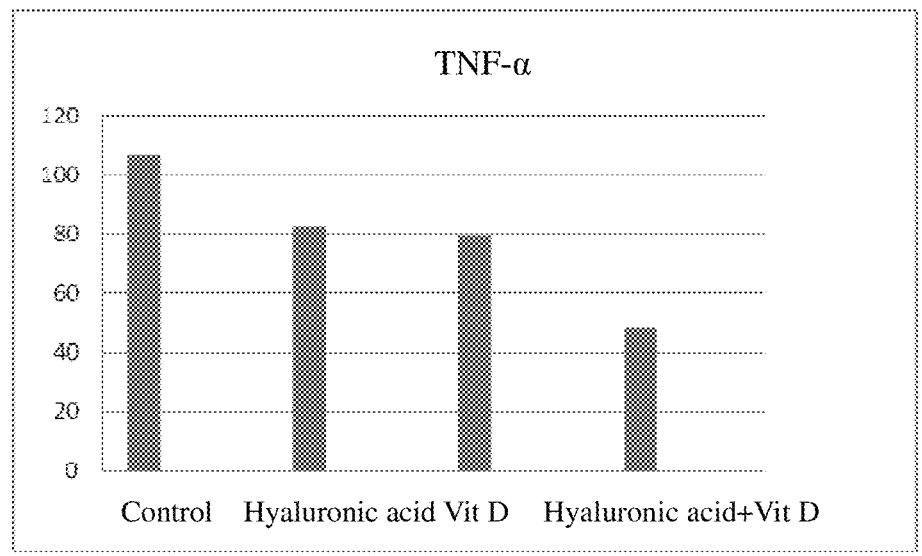
FIG. 3 is a statistic column diagram showing the expression level of TNF-α in the fibroblast-like synoviocytes treated by vitamin D.
Figure 4:
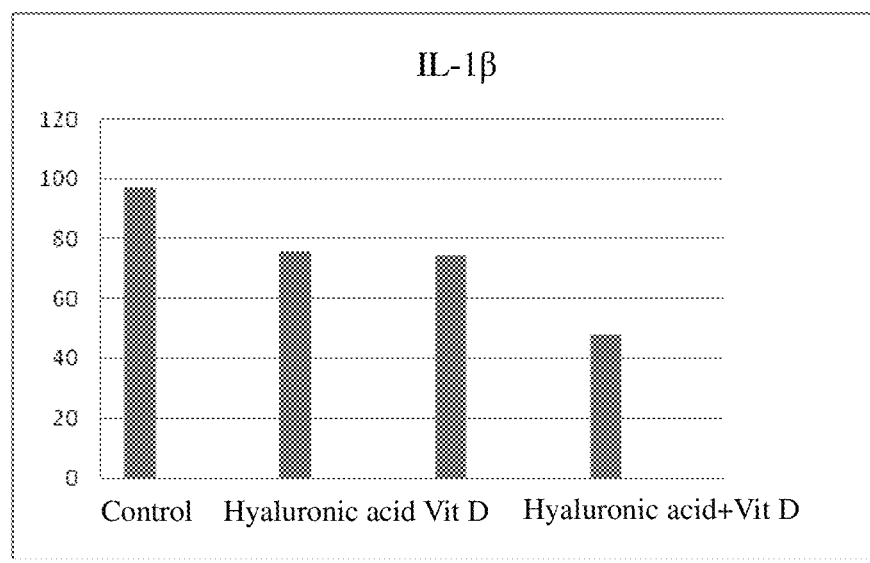
FIG. 4 is a statistic column diagram showing the expression level of IL-1β in the fibroblast-like synoviocytes treated by vitamin D.
Figure 5:
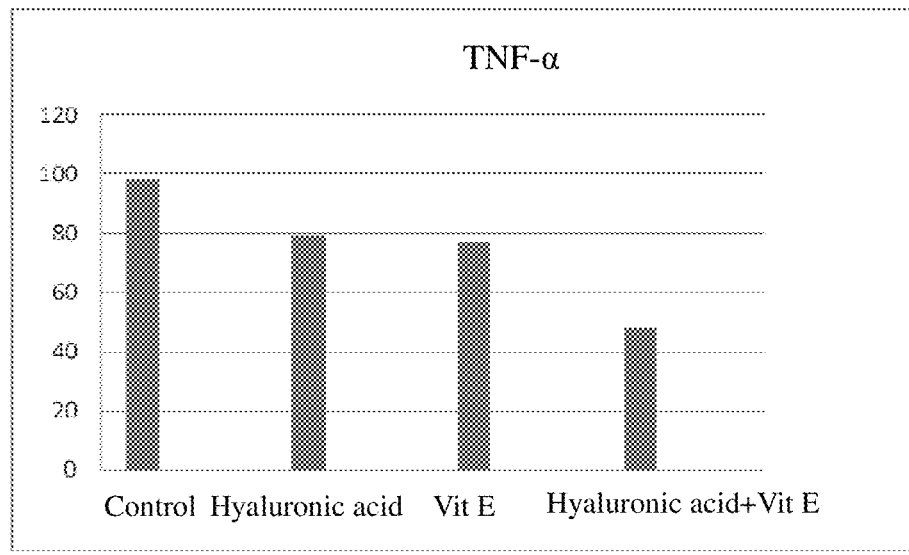
FIG. 5 is a statistic column diagram showing the expression level of TNF-α in the fibroblast-like synoviocytes treated by vitamin E.
Figure 6:
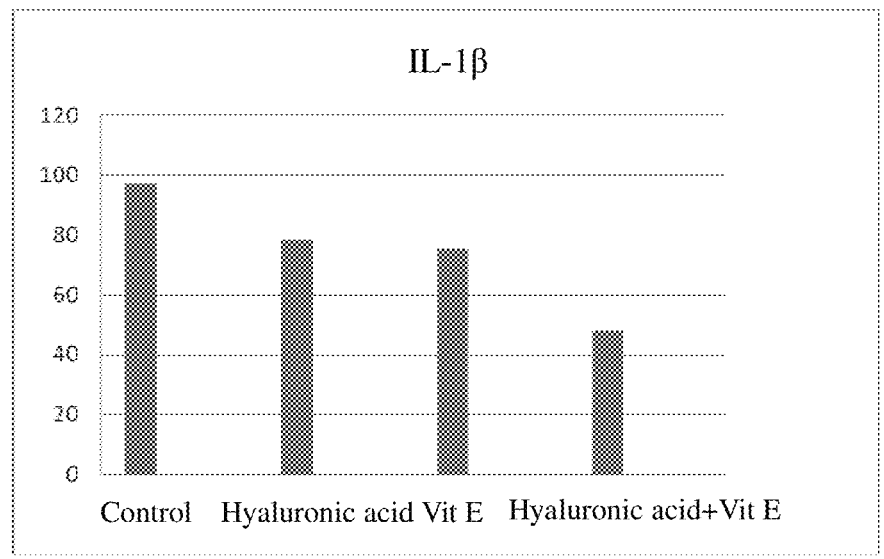
FIG. 6 is a statistic column diagram showing the expression level of IL-1β in the fibroblast-like synoviocytes treated by vitamin E.

The results in Tables 1 to 3 and FIGS. 1 to 6 show that the joint cells from the patients with degenerative arthritis secreted a large amount of the inflammation mediators, TNF-α and IL-1β, indicating that severe inflammation had occurred. However, a combination of hyaluronic acid and vitamin can effetely inhibit the expression of the inflammation mediators. As shown in FIGS. 1, 3, and 5, the combination of hyaluronic acid and vitamins of the present invention can effectively inhibit the expression of TNF-α (an important pathogenic factor of rheumatoid arthritis), and thus, it can provide an excellent inhibition effect on arthritis, especially on rheumatoid arthritis. In addition, as shown in FIGS. 2, 4, and 6, by inhibiting the expression of IL-1β, the combination of hyaluronic acid and vitamin of the present invention also can provide an inhibition effect on inflammation, especially on degenerative arthritis. The above analysis data also indicates that the pharmaceutical composition of the present invention can provide an improved effect on anti-inflammation.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A method for inhibiting arthritis in a subject in need thereof, comprising administering to the subject an effective amount of a pharmaceutical composition consisting of (a) hyaluronic acid, (b) a vitamin and (c) a pharmaceutically acceptable carrier, wherein the component (b) is vitamin D, and the component (a) and component (b) are present at a weight ratio of component (a)/component (b)=about 1,000/1 to about 100,000/1; wherein the pharmaceutical composition is administered by intra-articular injection.

2. The method as claimed in claim 1, wherein the component (a) has an average molecular weight ranging from about 30,000 Daltons to about 10,000,000 Daltons.

3. The method as claimed in claim 1, wherein the component (a) has an average molecular weight ranging from about 500,000 Daltons to about 6,000,000 Daltons.

4. The method as claimed in claim 1, which is for inhibiting osteoarthritis, rheumatoid arthritis, or gouty arthritis.

5. The method as claimed in claim 4, which is for inhibiting rheumatoid arthritis.

* * * * *